United States Patent [19]

Farbood et al.

[11] Patent Number: 4,970,163
[45] Date of Patent: Nov. 13, 1990

[54] PROCESS FOR PRODUCING DIOL AND LACTONE AND MICROORGANISMS CAPABLE OF SAME

[75] Inventors: Mohamad I. Farbood, Holmdel; James A. Morris, Wall; Arthur E. Downey, Linden, all of N.J.

[73] Assignee: International Flavors & Fragrances Inc., New York, N.Y.

[21] Appl. No.: 399,826

[22] Filed: Aug. 28, 1989

[51] Int. Cl.$^5$ .................. C12N 1/16; C12P 17/02; C12P 17/04; C12P 7/00
[52] U.S. Cl. ..................... 435/255; 435/123; 435/126; 435/127; 435/132; 435/144; 435/156; 435/911
[58] Field of Search ............... 435/911, 123, 125, 132, 435/156, 254, 255, 148, 124, 126, 171, 127; 514/449, 451, 454, 455

[56] References Cited

U.S. PATENT DOCUMENTS

| | | | |
|---|---|---|---|
| 3,905,868 | 9/1975 | Hamsher | 435/44 |
| 4,441,514 | 4/1984 | Mitchell et al. | 131/276 |
| 4,798,799 | 1/1989 | Farbood et al. | 435/254 |

OTHER PUBLICATIONS

Lodder et al., *The Yeasts*, 1970 pp. 1088–1127.
de Hoog et al., Antonie van Leeuwenhoek 52, 1986, p. 39–44.
Kockova-Kratochvilova et al., *Ceska Mykol.* vol. 38, (1), 1989, p. 11–20.

*Primary Examiner*—Elizabeth C. Weimar
*Assistant Examiner*—Irene Marx
*Attorney, Agent, or Firm*—Arthur L. Liberman

[57] ABSTRACT

Described is a microbilogical method for producing the lactone, sclareolide and a diol having the chemical structure:

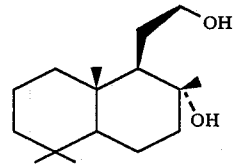

using sclareol having the structure:

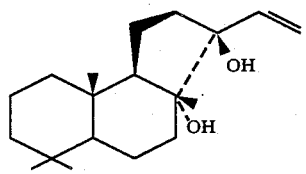

as a substrate and using one of the microorganisms:
Cryptococcus albidus (saito [skinner var. albidus]), ATCC 20918
Bensingtonia ciliata, ATCC 20919
Cryptococcus laurentii, ATCC 20920
Cryptococcus albidus, ATCC 20921.

8 Claims, 4 Drawing Sheets

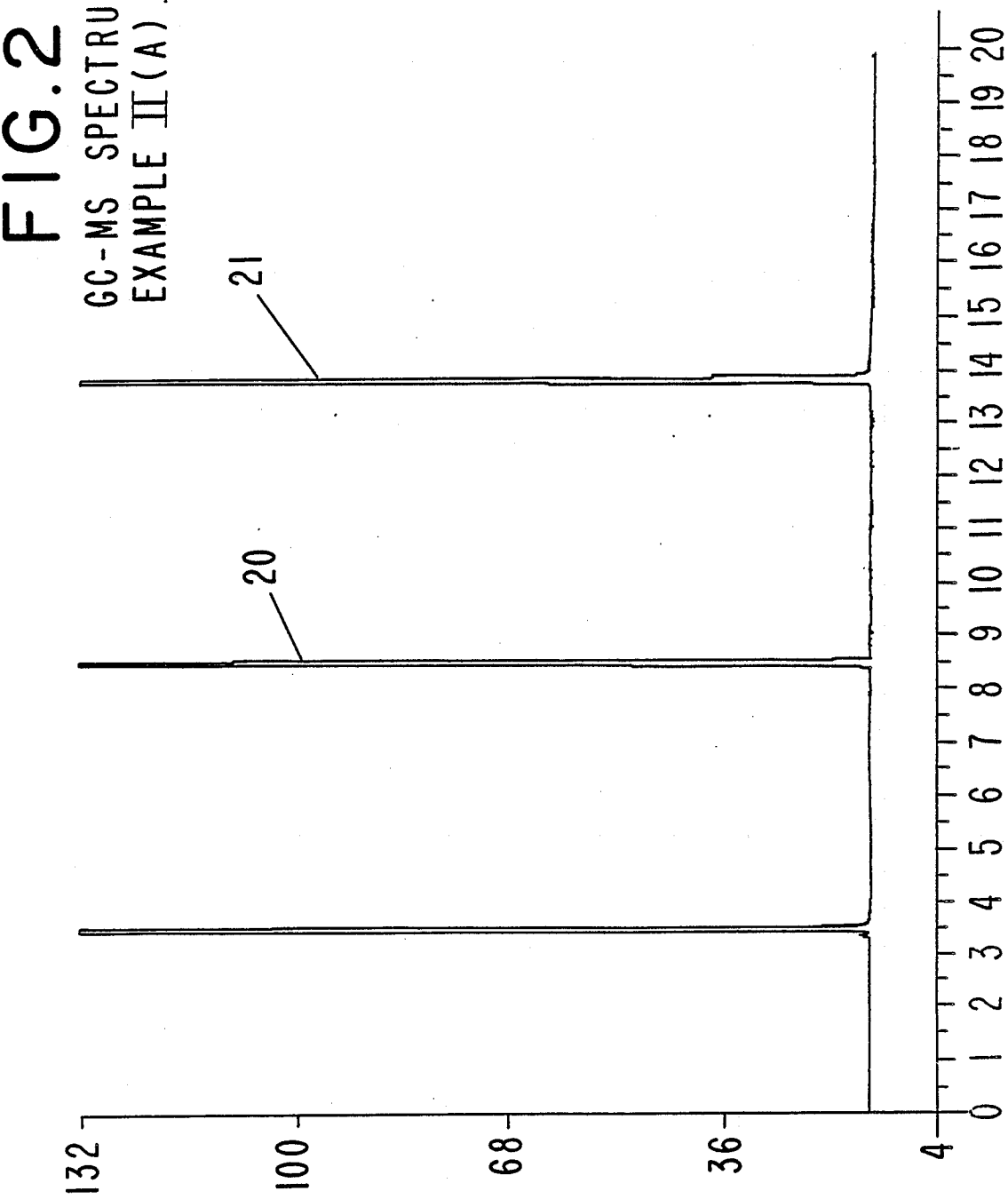

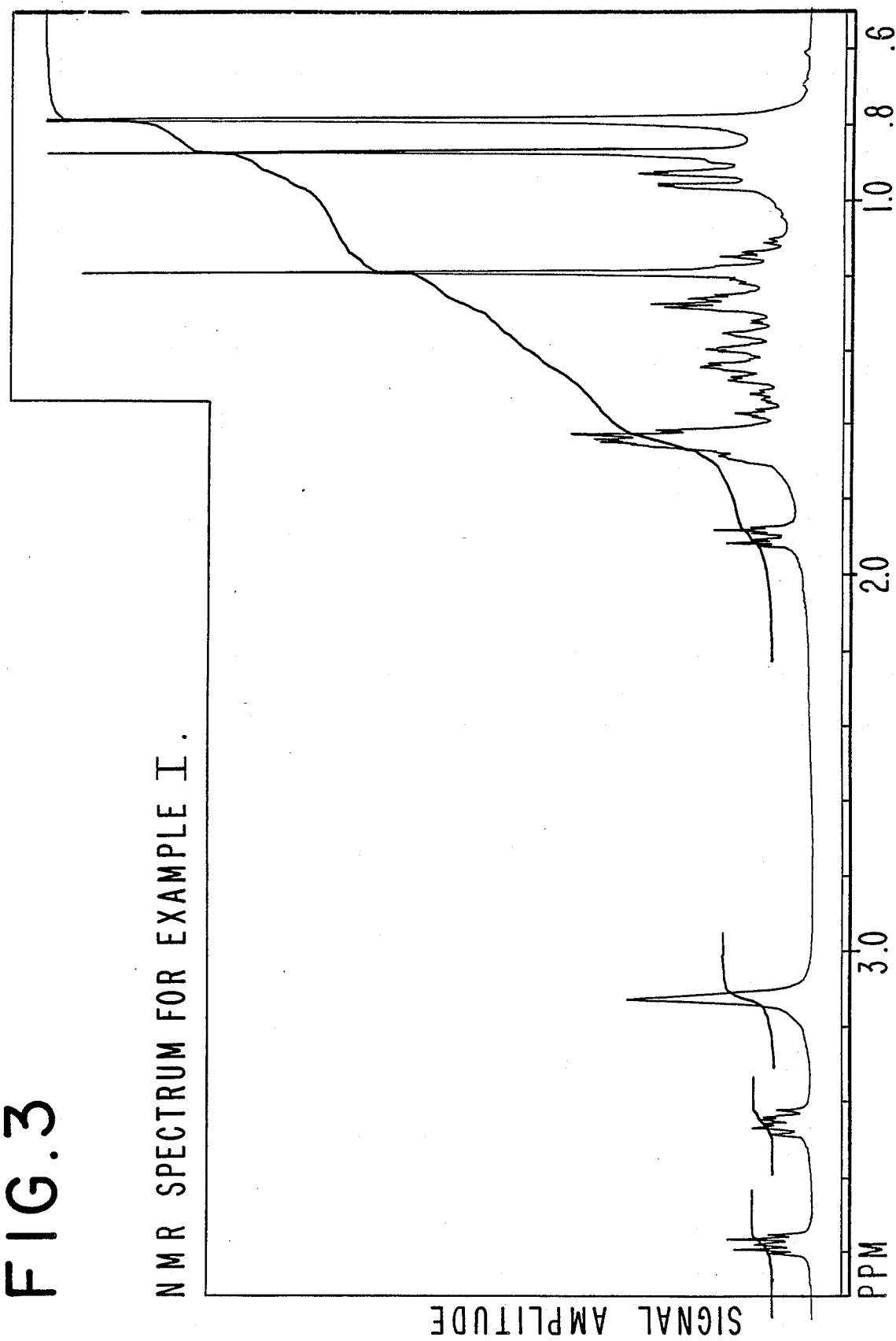
FIG. 3 NMR SPECTRUM FOR EXAMPLE I.

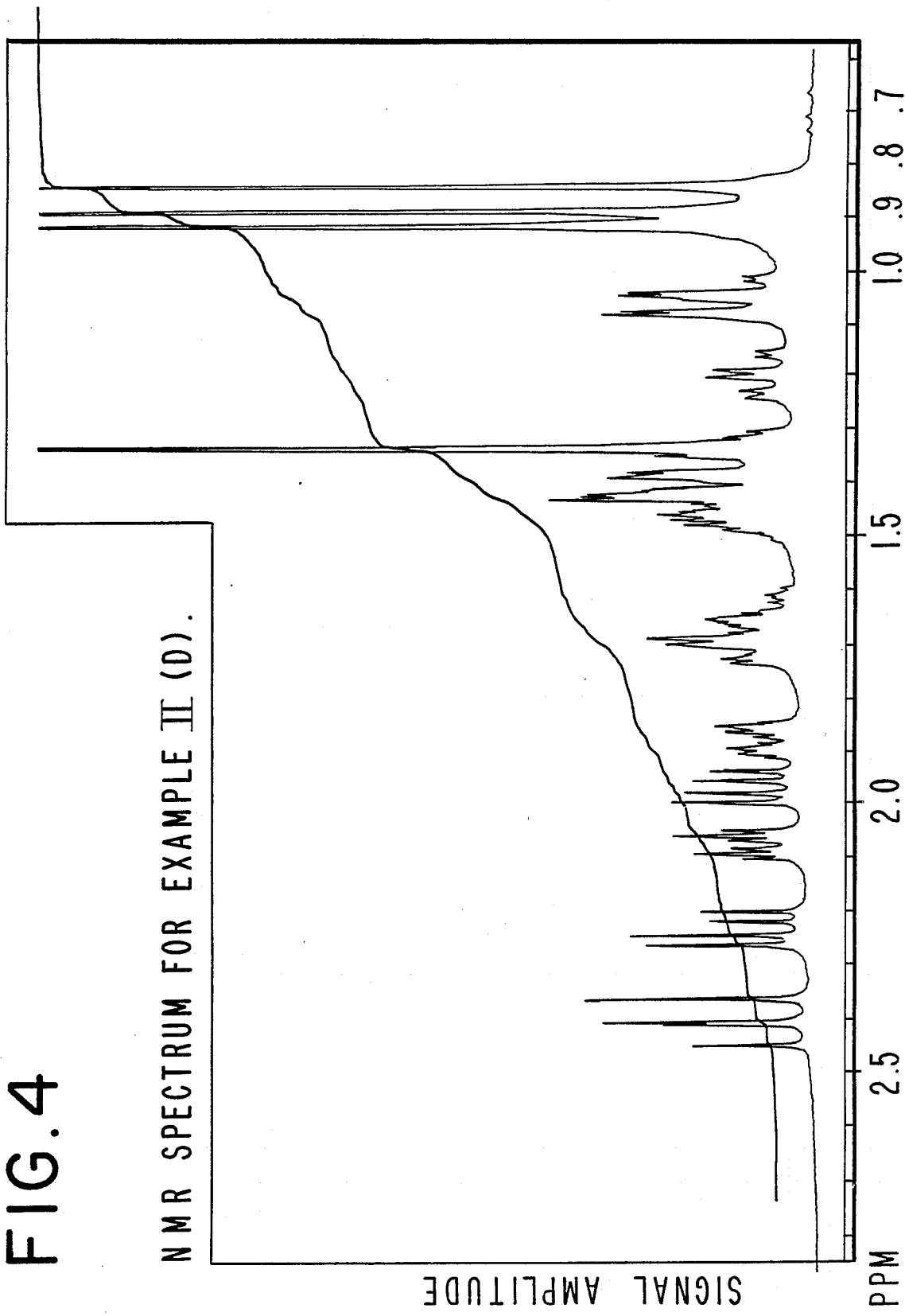

PROCESS FOR PRODUCING DIOL AND LACTONE AND MICROORGANISMS CAPABLE OF SAME

BACKGROUND OF THE INVENTION

The compound sclareolide having the structure:

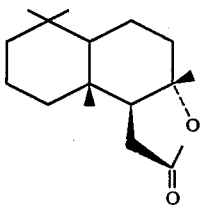

has been found to be a valuable intermediate in preparing the compound having the structure:

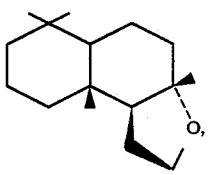

an important material for use in perfumery.

The compound having the structure:

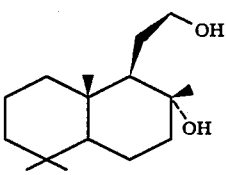

has been shown to be useful in U.S. Pat. No. 4,798,799 issued Jan. 17, 1989 as an intermediate in the creation of the compound having the structure:

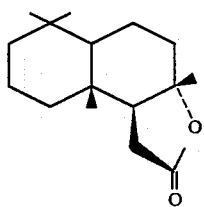

and has been also shown to be useful precursor of the compound having the structure:

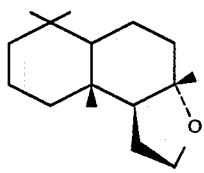

at column 8, lines 58-60 of U.S. Pat. No. 4,798,799.

Indeed, U.S. Pat. No. 4,798,799 discloses the utilization of a culture containing the microorganism *Hyphozyma roseoniger* having the identifying characteristics of CBS 214.83 and ATCC 20624 capable of producing the diol having the structure:

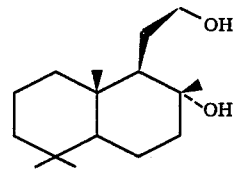

in a recoverable quantity upon the transformation of compounds including the compound having the structure:

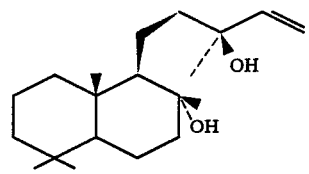

(sclareol). Table IV, thereof at column 12, lines 15-28 discloses yields of 96% when carrying out the reaction:

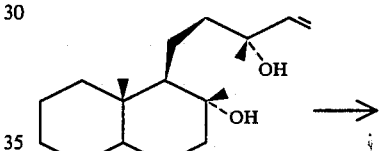

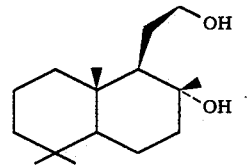

under fermentation conditions using ATCC 20624.

There is no teaching or suggestion in the prior art of either (a) carrying out the reaction:

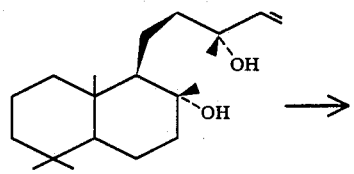

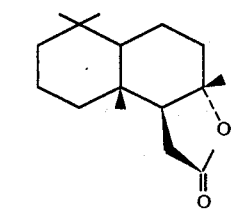

via microbiological methods whereby the compound having the structure:

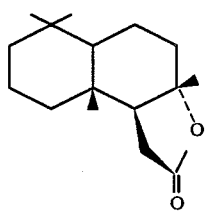

is formed in relatively high yields or (b) carrying out the reaction:

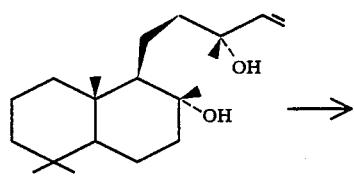

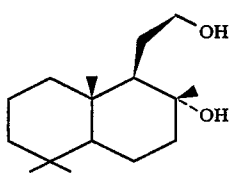

via a microbiological method using the organism *Bensingtonia ciliata*, ATCC 20919 or *Cryptococcus laurentii*, ATCC 20920.

Furthermore, the organisms:
*Cryptococcus albidus*, ATCC 20918;
*Bensingtonia ciliata*, ATCC 20919;
*Cryptococcus laurentii*, ATCC 20920; and
*Cryptococcus albidus*, ATCC 20921
are novel organisms.

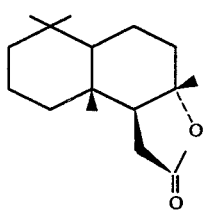

Figure 1:
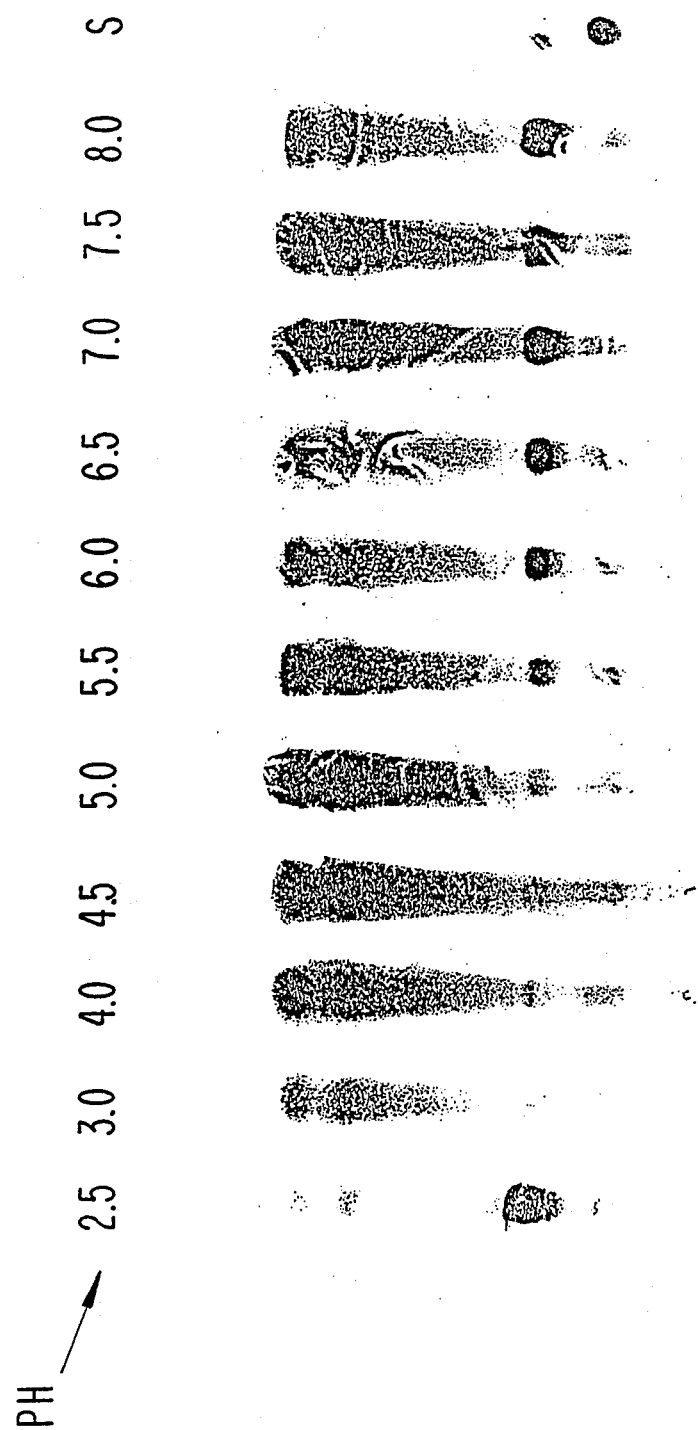
FIG. 1 is a photocopy of the thin layer chromatography eluates of the product of Example A versus pH using *Cryptococcus albidus* (ATCC 20918) whereby sclareolide having the structure.

and the diol intermediate having the structure:

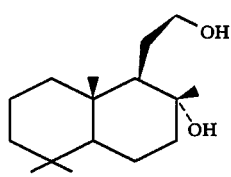

are formed from sclareol having the structure:

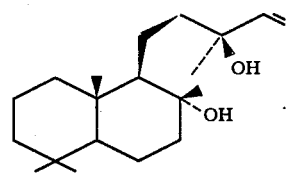

(the substrate)).

FIG. 2 is a GC-MS spectrum for the starting material of Example II(A). The peak indicated by reference numeral 21 is the peak for the peak for the crude sclareol having the structure:

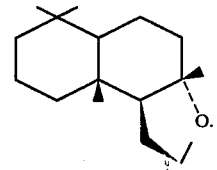

The peak indicated by reference numeral 20 is the peak for the internal standard, for the compound having the structure:

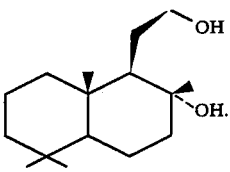

FIG. 3 is the NMR spectrum for the reaction product of Example I, the compound having the structure:

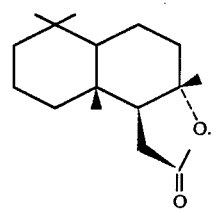

FIG. 4 is the NMR spectrum for the reaction product of Example II(D) having the structure:

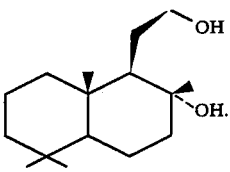

SUMMARY OF THE INVENTION

The present invention concerns biologically pure cultures of the microorganisms:
*Cryptococcus albidus*, ATCC 20918 (saito [skinner var. albidus])
*Bensingtonia ciliata*, ATCC 20919; and
*Cryptococcus laurentii*, ATCC 20920; and

*Cryptococcus albidus*, ATCC 20921.

In another embodiment the present invention concerns cultures containing the microorganisms:

*Cryptococcus albidus*, ATCC 20918 (saito [skinner var. albidus])
*Bensingtonia ciliata*, ATCC 20919;
*Cryptococcus laurentii*, ATCC 20920; and
*Cryptococcus albidus*, ATCC 20921,
said cultures individually capable of producing either the diol having the structure:

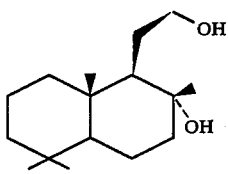

or sclareolide having the structure:

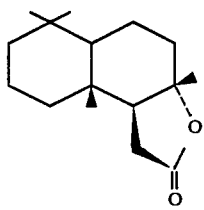

as follows:
*Cryptococcus albidus*, ATCC 20918 (saito [skinner var. albidus]) and
*Cryptococcus albidus*, ATCC 20921,
capable of producing sclareolide having the structure:

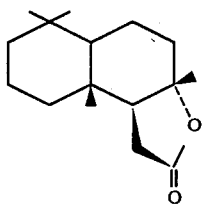

from a mixture of sclareol having the structure:

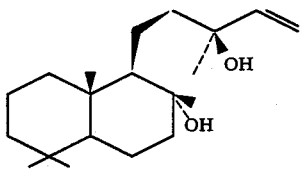

and episclareol having the structure:

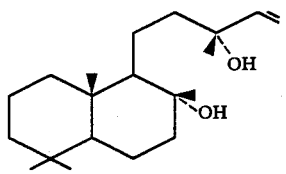

*Bensingtonia ciliata*, ATCC 20919 and *Cryptococcus laurentii*, ATCC 20920 capable of producing the diol having the structure:

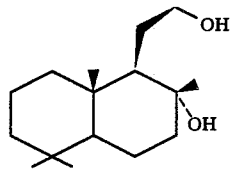

from a mixture of sclareol having the structure:

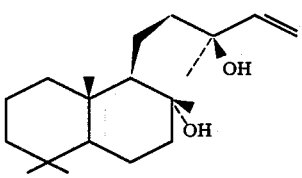

and episclareol having the structure:

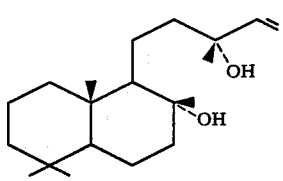

under aerobic conditions in an aqueous nutrient medium.

In still another embodiment the present invention concerns mixtures prepared by cultivating the microorganisms (individually) as follows:

*Cryptococcus albidus* (saito [skinner var. albidus]) having the identifying characteristics of ATCC 20918;
*Bensingtonia ciliata* having the identifying characteristics of ATCC 20919;
*Cryptococcus laurentii* having the identifying characteristics of ATCC 20920; and
*Cryptococcus albidus* having the identifying characteristics of ATCC 20921
under aerobic conditions in an aqueous nutrient medium.

In a further embodiment the present invention concerns:

(i) a process for preparing sclareolide having the structure:

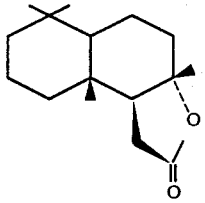

which comprises cultivating either the organism *Cryptococcus albidus* (saito [skinner var. albidus]) having the identifying characteristic of ATCC 20918 or *Cryptococcus albidus* having the identifying characteristic of ATCC 20921 under aerobic conditions in a aqueous nutrient medium containing one or more of the compounds having the structures:

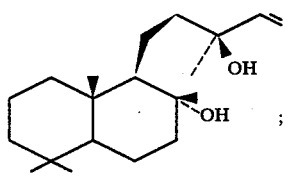

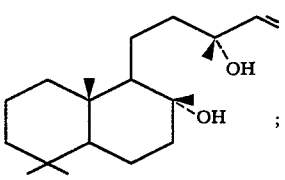

and/or

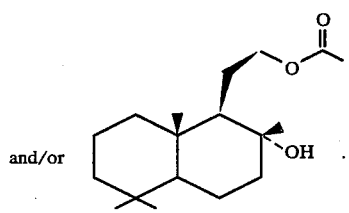

In still a further embodiment the present invention concerns processes for preparing the diol having the structure:

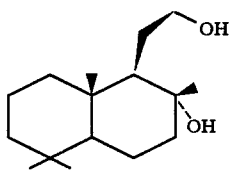

which comprises cultivating either of the microorganisms:

(a) *Bensingtonia ciliata* having the identifying characteristics of ATCC 20919; or (b) *Cryptococcus laurentii* having the identifying characteristics of ATCC 20920 under aerobic conditions in a aqueous nutrient medium containing one or more of the compounds selected from the group consisting of:

(i) sclareol having the structure:

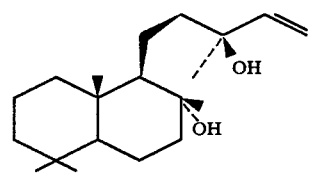

(ii) episclareol having the structure:

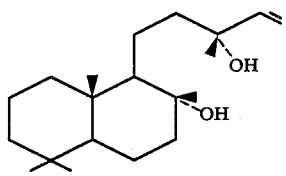

(iii) the acetate having the structure:

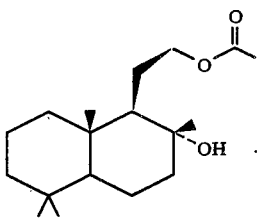

The transformation processes involve cultivation of one of the microorganisms:

*Cryptococcus albidus* (saito [skinner var. albidus]), ATCC 20918;

*Bensingtonia ciliata*, ATCC 20919;

*Cryptococcus laurentii*, ATCC 20920; or

*Cryptococcus albidus*, ATCC 20921 in aqueous nutrient medium in the presence of one, two or all of the compounds having the structures:

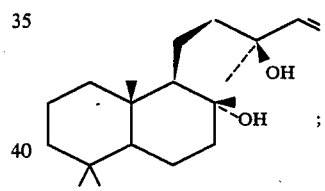

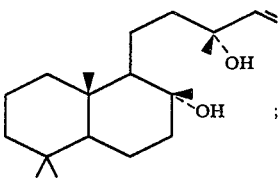

and

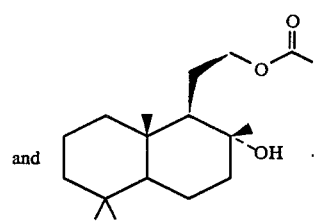

Thus, these compounds may be used singularly or as a mixture containing any number of said compounds.

Thus, in carrying out the reaction using:

*Cryptococcus albidus* (saito [skinner var. albidus]), ATCC 20918 or

*Cryptococcus albidus*, ATCC 20921 the following reactions can take place:

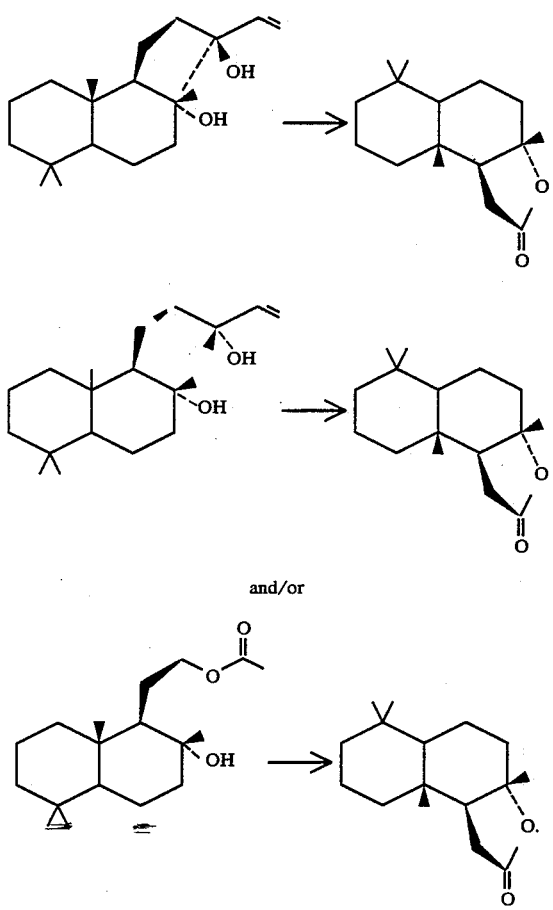

In carrying out the reactions using *Bensingtonia ciliata*, ATCC 20919 or *Cryptococcus laurentii*, ATCC 20920 the following reactions can take place:

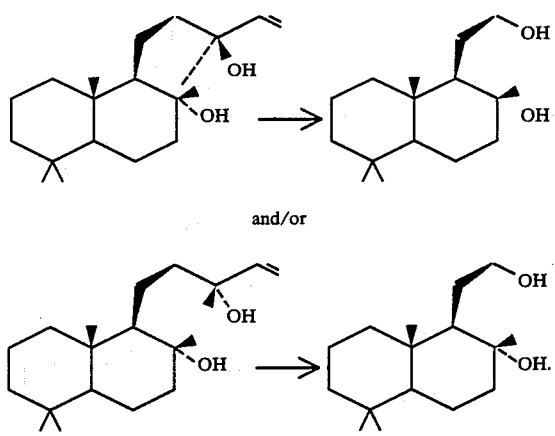

The form in which the microorganisms are used is not critical. They can be used as the culture (suspension), i.e., including the cells and the corresponding nutrient solution, or in the form of cells suspended in a buffer solution. The cells, or an enzyme extract thereof, may be immobilized on a suitable solid support, which may then be used to effect transformations.

The suspended culture mixture is prepared by inoculation of a suitable aqueous nutrient medium with the microorganisms. A suitable nutrient medium is one which contains nitrogen sources, inorganic salts, growth factors, the desired substrate(s), and optionally other carbon sources. Some carbon sources suitable for use in the inventive process include, for example, glucose, galactose, L-sorbose, maltose, sucrose, cellobiose, trehalose, L-arabinose, L-rhamnose, ethanol, glycerol, L-erythrithol, D-mannitol, lactose, melibiose, raffinose, melezitose, starch, D-xylose, D-sorbitol, a-methyl-D-glucoside, lactic acid, citric acid and succinic acid. Suitable nitrogen sources include, for example, nitrogen-containing organic substances such as peptone, meat extract, yeast extract, corn steep liquor, casein, urea, amino acids, or nitrogen-containing inorganic compounds such as nitrates, nitrites and inorganic ammonium salts. Suitable inorganic salts include, for example, phosphates of magnesium, potassium, calcium, or sodium. The above mentioned culture medium nitrients may be supplemented with, for example, one or more vitamins of the B group and/or one or more trace minerals such as Fe, Mo, Cu, Mn, and B, as desired. The Vitamins of trace minerals are not necessary when a small amount of yeast extract is added to the medium. Addition of an antibiotic, such as chloroamphinical or chlorotetracycline, may be desirable when bacterial contamination is a problem.

The cultivation of the microorganism may be carried out as a stationary culture or as a submersed (e.g., shaking culture, fermentor culture) under aerobic conditions. One may suitably work in the pH range of from between about 2.5 and about 9.0, and preferably in the range of from between about 3.0 and about 7.5 and most preferably between about 3.0 and 6.5. The pH may be regulated by the addition of inorganic or organic acids, such as hydrochloric acid, acetic acid, and oxalic acid, or by the addition of bases, such as sodium hydroxide, and ammonium hydroxide, or by the addition of a buffer, such as phosphate or phthalate. The incubation temperature should suitably be maintained between about 12° C. and about 33° C., with a range between about 15° C. and about 30° C. being more preferred, and a range between about 18° C. and about 28° C. being most preferred.

The process in accordance with this invention may be conveniently carried out by adding one or a mixture of the compounds having the structures:

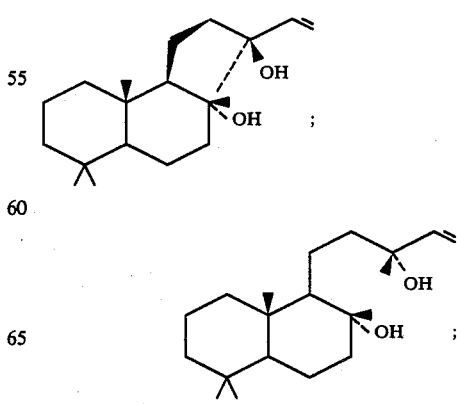

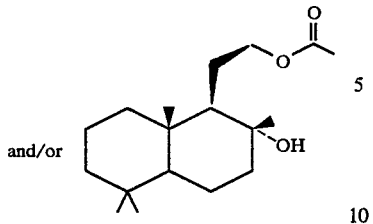
and/or to the nutrient medium at the onset of cultivation, as the sole carbon source. Alternatively, the substrate may be added in combination with another carbon source, such as dextrose, either during cultivation, or when the carbon source is depleted. The only restriction on the concentration of substrate in the culture medium is that of being able to effectively aerate the culture. However, the substrate concentration is preferably in the range of between about 0.1 g/L and about 100 g/L, more preferably in the range of between about 0.5 g/L and about 50 g/L, and most preferably in the range between about 2.5 g/L about 30 g/L. The transformation can be suitably carried under any of the above mentioned conditions.

The total transformation time (after initial cultivation period) may vary depending on the composition of the nutrient medium and the substrate concentration. In general, shaking flask cultures require from between about 12 hours and about 264 hours. However, when a fermentor is used the cultivation time may be reduced to about 48 hours or less.

The transformation may be carried out using the cells of the microorganism isolated from the culture solution, with with an enzyme extract isolated from the cells in a manner well known to the art. In this case, the transformation can be conveniently carried out in a variety of aqueous nutrient mediums including, for example, in a buffer solution, in a physiological salt solution, in a fresh nutrient solution, or in water. The isolated cells or enzyme extract may be immobilized on a solid support and the desired transformation effected. Also, transformation of the substrate may be effected by mutants of this organism. Such mutants can be readily obtained by methods well known in the art, for example, by exposing the cells to UV or X-rays, or known mutagenic substances, such as, for example, acridine orange.

The substrate can be added to the medium as a powder, or a slurry in an emulsifier such as TWEEN ® 80 (polyoxyethylenesorbitan monstearate), or as a solution in an emulsifier, or as a solution in a hydrophilic solvent such as acetone, methanol, ethanol, ethylene glycol, or dioxan. A surface-active agent, or a dispersion agent can also be added to an aqueous suspension of the substrate, or the substrate can be emulsified using ultrasound.

Conventional antifoam agents, such as silicone oils (e.g., UCON), polyalkyleneglycol derivatives, maize oil, or soya oil, can be used to control foaming.

The transformation of the substrate can be monitored using standard analytical techniques such as GLC, TLC, HPLC, IR and NMR. If a rapid disappearance of the substrate is observed more substrate can then be added, in order to maximize the transformation capacity of the microorganism. The process is generally terminated when most of the substrate has disappeared from the culture medium. Depending upon the microorganism used, the compound having the structure:

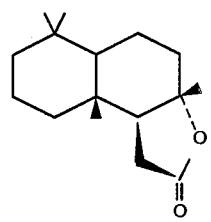

or the compound having the structure:

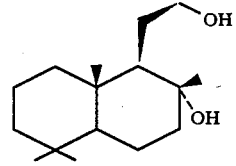

may be recovered from the aqueous nutrient medium. The compound having the structure:

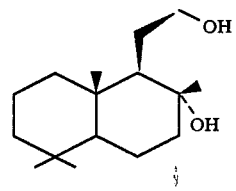

may be cyclized to the compound having the structure:

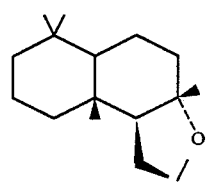

as stated at lines 52 and 53, at column 8 of U.S. Pat. No. 4,798,799 the specification for which is incorporated by reference herein. The compound having the structure:

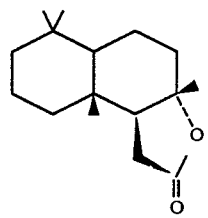

may also be used as is for its flavor or fragrance values or it may be reduced to the compound having the structure:

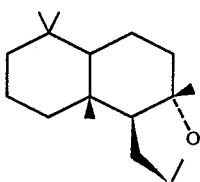

according to the reaction:

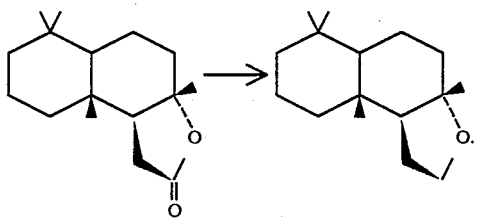

Isolation and purification of the compounds having the structures:

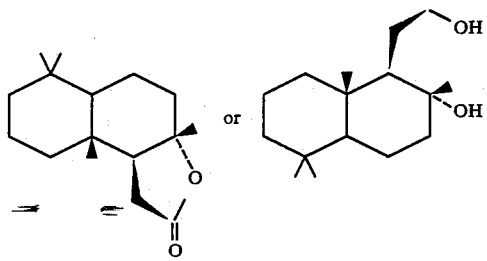

from the fermentation broths may be achieved by conventional techniques including, filtration orcentrifugation, solvent extraction, distillation, crystallization, and the like.

The compound having the structure:

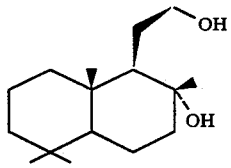

may be converted to the compound having the structure:

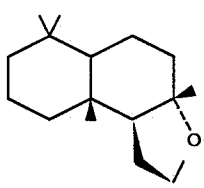

by conventional cyclization methods well known in the art as specified at lines 58–68, at column 8 of U.S. Pat. No. 4,798,799 and at column 9, lines 1 and 2 of U.S. Pat. No. 4,798,799.

Each of the microorganisms employed in this invention was isolated from a soil samples obtained from Central New Jersey, United States of America. Each of the strains has been deposited with the American Type Culture Collection with the accession numbers as follows:

*Cryptococcus albidus* (saito [skinner var. albidus]), ATCC 20918;
*Bensingtonia ciliata*, ATCC 20919;
*Cryptococcus laurentii*, ATCC 20920; and
*Cryptococcus albidus*, ATCC 20921.

The organisms *Bensingtonia ciliata* and *Cryptococcus laurentii* were also studied by Centralbureau voor Schimmel Cultures (CBS). CBS assigned both of these organisms the name:

*Lecythophere hoffmannii* (van Beijma), W. Gams (synonym *Phialophora hoffmannii*)

because this is a filamentous fungus according to CBS.

The organism *Cryptococcus albidus* (saito [skinner var. albidus]), ATCC 20918 is described as follows:

Morphology: Growth in liquid medium showed unipolar budding cells. A film stayed on the surface of the liquid while heavy sediment was observed. Growth on solid agar was unicellular with colonies being white to slightly pinkish, very shiny, bright, slimy, round and with smooth borders. No pseudohyphae were formed on corn meal aga.

| Physiology and Biochemistry: | | | |
|---|---|---|---|
| Carbon Assimilation: (Growth) | | Carbon Assimilation: (Growth) | |
| Glucose | + | D-ribose | U |
| Galactose | + | L-rhamnose | + |
| L-sorbose | + | D-glucosamine | + |
| Maltose | + | Ethanol | U |
| Sucrose | + | Erythritol | − |
| Cellobiose | + | Glycerol | U |
| Trehalose | + | Adonitol (Ribitol) | + |
| Lactose | + | Dulcitol (Galactitol) | + |
| Melibiose | − | D-mannitol | + |
| Raffinose | + | D-sorbitol (glucitol) | + |
| Melezitose | + | a-methyl-D-glucoside | + |
| Inulin | − | Salicin | + |
| Soluble Starch | − | Inositol | + |
| D-xylose | − | Lactic acid | − |
| L-arabinose | − | Citric acid | − |
| D-arabinose | − | | |
| Succinic acid | + | | |
| Growth at 30° C. | + | | |
| Growth at 37° C. | − | | |
| Vitamin free growth | − | | |
| Splitting of arbutin | + | | |
| Nitrogen assimilation: | | | |
| NH₄NO₃ | + | | |
| KNO₃ | + | | |
| NO₂ | + | | |
| Ethylamine | + | | |
| Fermentation (Acid from): | | | |
| Glucose | − | | |
| Galactose | − | | |
| Maltose | − | | |
| Sucrose | − | | |
| Lactose | − | | |
| Raffinose | − | | |
| Melibiose | − | | |
| Inulin | − | | |
| Cellobiose | − | | |
| Melezitose | − | | |
| Starch | − | | |
| Trehalose | − | | |

Note:
U = undecided or questionable

The organism *Bensingtonia ciliata*, ATCC 20919 is described as follows:

Morphology: One Yeast Maintenance Broth (ATCC medium #200) cells are globose with 1-3 buds per cells. On solid medium cells become filamentous with ballistospores produced. Colonies are tan-salmon in color, flat, dull, with smooth edges. On Corn Meal Agar (ATCC medium #307) true mycelium were noticed after 3 weeks.

| Physiology: | | | |
|---|---|---|---|
| Carbon Assimilation: | | Carbon Assimilation: | |
| Glucose | + | D-ribose | − |
| Galactose | + | L-rhamnose | + |
| L-sorbose | + | D-glucosamine | + |
| Maltose | + | Ethanol | W |
| Sucrose | + | Erythritol | + |
| Cellobiose | + | Glycerol | + |
| Trehalose | + | Adonitol (Ribitol) | W |
| Lactose | − | Dulcitol (Galactitol) | W |
| Melibiose | + | D-mannitol | W |
| Raffinose | + | D-sorbitol (glucitol) | W |
| Melezitose | + | a-methyl-D-glucoside | W |
| Inulin | − | Salicin | W |
| Soluble Starch | + | Inositol | − |
| D-xylose | + | Lactic acid | − |
| L-arabinose | + | Citric acid | − |
| D-arabinose | − | Succinic acid | W |
| Vitamin free growth | − | | |
| Nitrogen assimiliation: | | | |
| NH4NO3 | W | | |
| Growth at elevated temp: | | | |
| 30° C. | W/− | | |
| 37° C. | − | | |

Note:
W = weak

Taxonomic Description: *Bensingtonia ciliata* C.T. Ingold Hyphomycete (Fungi Imperfecti).

A ballistosporic fungus (Spores forcibly abjected).

The ballistospores are colorless, avoid, 2×5 μm, mostly 8×5 μm in liquid culture, pointed at the apex and with a flattened base.

The ballistospores germinate with the formation of yeast-like blastospores that upon repeated spore formation results in typical yeast colonies (see photo).

Some ballistospores germinate with the formation of short hyphae that produces ballistospores and with repeated spore discharge results in colonies entirely of the hyphae type (see photo).

Evaluation from the following media:

| ATCC medium | | |
|---|---|---|
| | #307 | Corn Meal Agar (Difco 0386) and ½ sstrength Corn Meal Agar |
| | #200 | Yeast Malt Agar (Difco 0712) |
| | #331 | Neuropora Agar (Difco 0321) |
| | #1245 | YEPD |
| | #324 | Malt Extract Agar (Difco 0024) |
| | #336 | Potato Dextrose Agar |
| | #343 | V-8 Juice Agar |

References:
1. Ingold, C. T. (1986) *Bensingtonia ciliata* Gen. et. sp. nov., Ballistoporic Fungus. Trans. Br. Mycol. Soc. 86(2): 325-328.
2. Ingold. C. T. (1988) Further Observations on *Bensingtonia ciliata*. Trans. Br. Mycol. Soc. 91(1): 162-166.

*Cryptococcus laurentii*, ATCC 20920 is described as follows:

| Physiology and Biochemistry: | | | |
|---|---|---|---|
| Carbon Assimilation: (Growth) | | | |
| Glucose | + | D-ribose | + weak |
| Galactose | + | L-rhamnose | + |
| L-sorbose | + weak | D-glucosamine | V |
| Maltose | + | Ethanol | + |
| Sucrose | + | Erythritol | + |
| Cellobiose | + | Glycerol | + |
| Trehalose | + | Adonitol (Ribitol) | + weak |
| Lactose | + weak | Dulcitol (Galactitol) | V |
| Melibiose | + | D-mannitol | + |
| Raffinose | + | D-sorbitol (glucitol) | + |
| Melezitose | + | a-methyl-D-glucoside | + |
| Inulin | + | Salicin | + |
| Soluble Starch | + | Inositol | + |
| D-xylose | + | Lactic acid | + |
| L-arabinose | + | Citric acid | + |
| D-arabinose | + weak | Succinic acid | + |
| Nitrogen Assimilation: | | | |
| NH4NO3 | + | | |
| KNO3 | + | | |
| NO2 | + | | |
| Ethylamine | + | | |
| Vitamin free growth | + | | |
| Splitting of arbutin | + | | |
| Fermentation (Gas Production): | | | |
| Glucose | − | | |
| Galactose | − | | |
| Maltose | − | | |
| Sucrose | − | | |
| Lactose | − | | |
| Raffinose | − | | |
| Melibiose | − | | |
| Inulin | − | | |
| Cellobiose | − | | |
| Melezitose | − | | |
| Starch | − | | |
| Trehalose | − | | |

Note:
V = variable.

Morphology: Pink slimy colonies; round budding cells, heavy sediment in flask; on Dalmau plate thin hypae was formed.

Reference: C. P. Kurtzman, Mycologia 65; p. 388-395, 1973.

*Cryptococcus albidus*, ATCC 20921 is described as follows:

| Physiology and Biochemistry: | | | |
|---|---|---|---|
| Carbon Assimilation: | | | |
| Carbon Assimilation: (Growth) | | | |
| Glucose | + | D-ribose | − |
| Galactose | + | L-rhamnose | + |
| L-sorbose | + | D-glucosamine | + |
| Maltose | + | Ethanol | V |
| Sucrose | + | Erythritol | − |
| Cellubiose | + | Glycerol | V |
| Trehalose | + | Adonitol (Ribitol) | V |
| Lactose | + | Dulcitol (Galactitol) | + |
| Melibiose | − | D-mannitol | + |
| Raffinose | + | D-sorbitol (glucitol) | + |
| Melezitose | + | a-methyl-D-glusocside | + |
| Inulin | − | Salicin | + |
| Soluble Starch | + | Inositol | + |
| D-xylose | + | Lactic acid | − |
| L-arabinose | + | Citric acid | − |
| D-arabinose | + | Succinic acid | + |
| Nitrogen Assimilation: | | | |
| NH4NO3 | + | | |
| KNO3 | + | | |
| NO2 | + | | |
| Ethylamine | + | | |
| Vitamin free growth | + | | |
| Splitting of arbutin | + | | |

-continued

| Physiology and Biochemistry: | |
|---|---|
| Fermentation (Gas Production): | |
| Glucose | — |
| Galactose | — |
| Maltose | — |
| Sucrose | — |
| Lactose | — |
| Raffinose | — |
| Melibiose | — |
| Inulin | — |
| Cellobiose | — |
| Melezitose | — |
| Starch | — |
| Trehalose | — |

Note:
V = variable.

Morphology: Yellowish-tan, slimy colonies; round budding cells; heavy sediment in the flask, no pseudomycelium or true mycelium.

The following examples serve to illustrate embodiments of the invention as it is now preferred to practice it but no way or meant to limit the scope thereof. Unless otherwise stated weights are in grams, temperatures are in degrees centigrade and pressure is in mm/Hg..

EXAMPLE A

Effect of pH on Conversion of Sclareol to Sclareolide Using *Cryptococcus Albidus* (Saito [Skinner Var. Albidus])

Reactions:

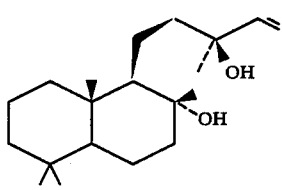
→ ⇌
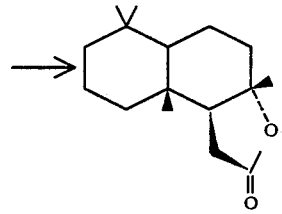

and

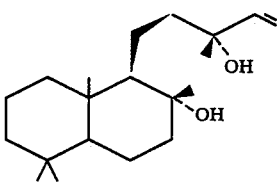
→
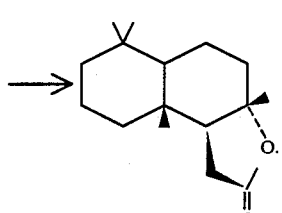

The following medium was prepared:

| NH₄NO₃ | 0.1% |
|---|---|
| KH₂PO₄ | 0.1% |
| MgSO₄.7H₂O | 0.05% |
| Yeast Extract | 0.2% |

11 Flasks were prepared. Each 500 ml flask contained 100 ml medium and 1 gram of sclareol paste in TWEEN® 80 (2:1).

Each flask was inoculated with 5 ml of a 24 hour grown cell culture in dextrose at 25° C. and 150 rpm. Product and substrate was monitored by TCL against a known standard.

In the following table the following codes are used:
TS: Trace Substrate
S: Substrate
TP: Trace Product
P: Product
I: Intermediate
TI: Trace Intermediate.

The "substrate" is sclareol which is an 80:20 mixture of the compound having the structure:

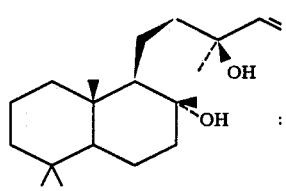

the compound having the structure:

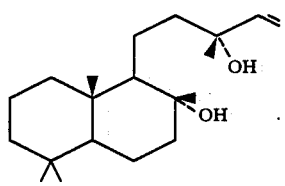

The "intermediate" is the compound having the structure:

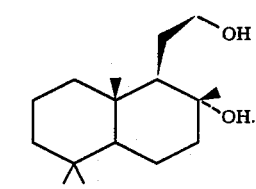

The "product" is the compound having the structure:

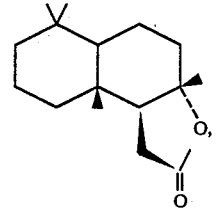

sclareolide.

TABLE I

| Flask No. | pH | Duration 24 Hours | Duration 48 Hours | Duration 72 Hours |
|---|---|---|---|---|
| 1 | 2.5 | TP + S + TI | P + S + I | P + S + TI |
| 2 | 3.0 | P + TS + I | P + S + I | P |
| 3 | 3.5 | P + TS + TI | P + TI | P |
| 4 | 4.0 | P + TS + I | P + TI | P + TI |
| 5 | 4.5 | P + TS + I | P + I | P + TI |
| 6 | 5.0 | P + TS + I | P + I | P + TI |
| 7 | 7.0 | P + S + I | P + I | P + I |
| 8 | 7.5 | P + S + I | P + I | P + I |

TABLE I-continued

| Flask No. | pH | Duration 24 Hours | Duration 48 Hours | Duration 72 Hours |
|---|---|---|---|---|
| 9 | 8.0 | P + S + I | P + TI + I | P + I |
| 10 | 8.5 | P + S + I | P + TS + I | P + I |
| 11 | 9.0 | P + S + I | P + TS + I | P + I. |

FIG. 1 sets forth the thin layer chromatographic eluates of product versus pH using *Cryptococcus albidus*, (ATCC 20918).

EXAMPLE I

Preparation of Diol Intermediate

Reactions:

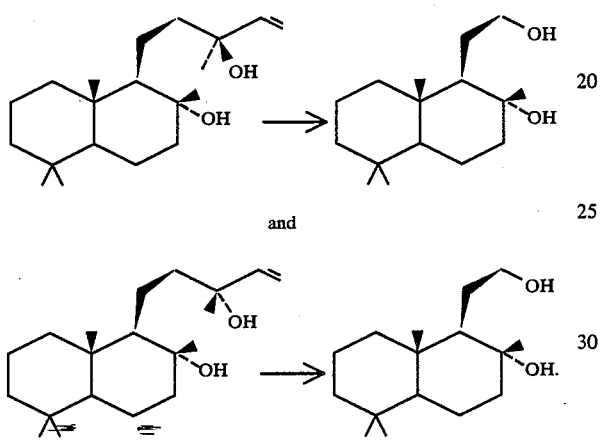

and

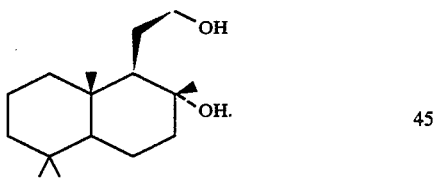

During screening of ten soil samples from Greenwood Forest, Barnegat Township, New Jersey several flasks showed a spot on the TLC corresponding to the compound having the structure:

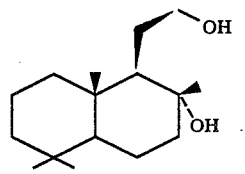

The following medium was prepared:

| | |
|---|---|
| NH₄NO₃ | 0.1% |
| KH₂PO₄ | 0.1% |
| MgSO₄.7H₂O | 0.05% |
| Yeast Extract | 0.2% |
| Agar | 2% |
| Dextrose | 1% |

Into a 500 ml flask was placed 100 ml medium and a 50:50 mixture of sclareol powder: TWEEN® 80. 1 Gram of the 50:50 sclareol: TWEEN® 80 mixture was added to the flask and inoculated with 400 micro liters of isolate of *Bensingtonia ciliata*, ATCC 20919. After one week at 25° C. and 150 rpm, the resulting product was extracted with 330 ml volumes of ethyl acetate and then dried over anhydrous sodium sulfite. The solvent was removed on a rotary evaporator. The residue was dissolved in hot hexane and ethyl acetate. The resulting extract is permitted to evaporate for a period of 24 hours whereupon pure crystals (350 mg) of the compound having the structure:

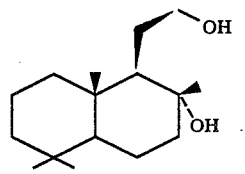

were recovered.

FIG. 3 is the NMR spectrum of the compound having the structure:

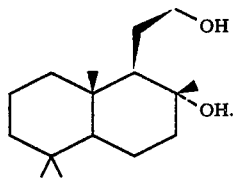

EXAMPLES II(A), II(B), II(C), II(D) AND II(F)

Preparation of Sclareolide from Sclareol Using *Cryptococcus Albidus* (Saito [Skinner var. Albidus]), ATCC 20918

Reactions:

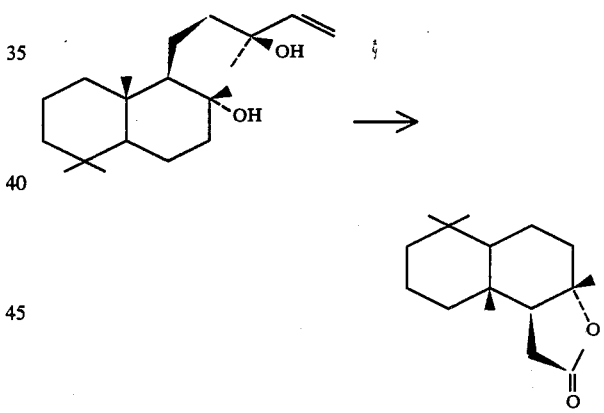

and

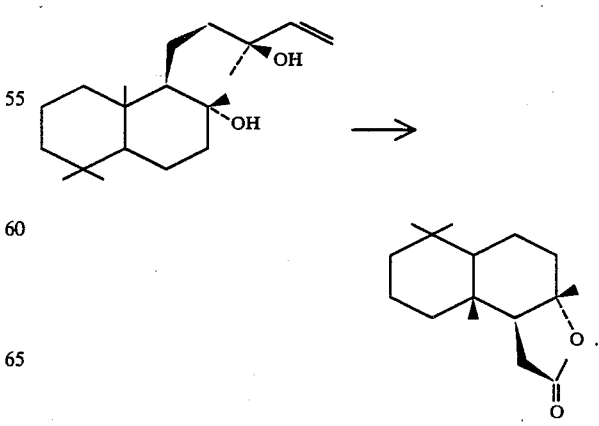

In each of the following examples, mixtures of sclareol and TWEEN ® 80 with water were prepared to form a sclareol paste. A fermentation broth was prepared containing the indicated amounts of:
NH₄NO₃
KH₂PO₄
MgSO₄.7H₂O
Yeast Extract
Antifoam Material ("AF")
Water.

The sclareol emulsion was added to the fermentation shake flask containing the fermentation medium and the cultures, *Cryptococcus albidus* (saito [skinner var. albidus]), ATCC 20918. At the end of the given period of time solid sclareolide having the structure:

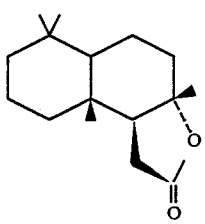

was recovered.

EXAMPLE II(A)

Sclareol preparation:

| Sclareol | 500 g |
| TWEEN ® 80 | 250 g |
| Water | 1125 g |
| | 1875 g | 0.27 g sclareol/g emulsion. |

600 g Emulsion — 160 g Sclareol.

| Broth | | Parameters |
|---|---|---|
| 20.0 g | NH₄NO₃ | 25° C. |
| 10.0 g | KH₂PO₄ | 1.02/min. |
| 5.0 g | MgSO₄.7H₂O | 0.2 |
| 20.0 g | Yeast Extract | 430 rpm |
| 10.0 g | AF | pH = 5.8:controlled w/25% NaOH |
| 8.5 | L-d-H₂O | |

Inoculation:
3 Fresh shake flask (100 ml/24 hr)
1 Old shake flask (100 ml)
Add 600 g emulsion of sclareol
600 of emulsion were added over the course of the fermentation up to a total of 2222 g emulsion or 600 g sclareol (60 g/L).
Final Recovery: 43 g/L sclareolide in 5 days.

EXAMPLE II(B)

Sclareol-Sclareolide:

Broth
7.5 L d-H₂O
18.0 g NH₄NO₃
9.0 g KH₂PO₆
4.5 g MgSO₄.7H₂O
18.0 g Yeast Extract
10.0 g AF

| 9/18 | |
|---|---|
| Inoculation: | 4% culture, 3-24 hr shake flask + 1 old flask. |
| Add: | 800 ml emulsion (0.25 g sclareol/ml) |
| | 200 g sclareol. |
| Aeration: | 0.8–1.0 L/min. |
| Agitation: | 430 rpm; 2nd day - 630 rpm. |
| Back Pressure: | 0.2 initially thru 0 on 2nd day. |
| Temp: | 25°. |
| P+: | 5.8 controlled w/25% NaOH. |
| 9/19 | Add 400 g emulsion 100 g sclareol = 300 g total |
| 9/20 | Add 600 ml emulsion 150 g sclareol = 450 g total |
| | Add 18 g NH₄NO₃ |
| 9/22 | Add 400 ml emulsion 100 g sclareol = 550 g total |
| 9/23 | Terminate; 7 hour w/o sterilization. |
| Results | |
| #1 - Crude: | 209 g @ 82.2% purity | 172 g |
| #2 - Crude: | 179 g @ 79.31% purity | 142 g |
| #3 - Crude: | 50.5 g @ 83.0% purity | 42 g |
| | 438.5 g | 356 g |

39.6 g/L Final Recovery.

EXAMPLE II(C)

| | (1) 20 L | (2) 10 L | (3) 10 L |
|---|---|---|---|
| | 200 g sclareol | 160 g sclareol | 160 g sclareol |
| | 100 g TWEEN ® 80 | 80 g TWEEN ® 80 | 80 g TWEEN ® 80 |
| | 40 g NH₄NO₃ | 20 g NH₄NO₃ | 20 g NH₄NO₃ |
| | 20 g KH₂PO₄ | 10 g KH₂PO₄ | 10 g KH₂PO₄ |
| | 10 g MgSO₄.7H₂O | 5 g MgSO₄.7H₂O | 5 g MgSO₄.7H₂O |
| | 40 g Yeast Extract | 20 g Yeast Extract | 20 g Yeast Extract |
| | 20 g AF | 10 g AF | 10 g AF |
| | 19.0 L Initial Vol. | 7.0 L Initial Vol. | 8.0 L Initial Vol. |

In all cases ingredients charged to fermentors and sterilization together.

Protocol:
(1) No additional sclareol; to be inoculated w/diol-producing organism.
(2) Additional sclareol to be added as suspension.
(3) Additional sclareol to be added as paste.
(2) and (3) Inoculation w/sclareolide-producing organisms.

Parameters:
25° C.
1.0 v/v/m; no back press.
630 rpm on 10 L; 250 rpm on 20 L.
pH 5.8 controlled w/25% NaOH.

Inoculation Preparation:

| 10 L | 500 ml grown on 1% sclareol | } = 64 hr. |
| 20 L | 1000 ml grown on 1% sclareol incubation. | |

3 Batches
(1) 20 L Batch was scrubbed - shaft seal failed; fermentation filled w/water.
(2) 8:15 Inoculation. Inoculation was somewhat light. Initial pH 5.52; set pH 5.8 DO 95%.
(3) 8:30 Inoculation (also light inoculation) Initial pH 5.54 set pH 5.8

-continued

|  |  |  |
|---|---|---|
|  | DO 95%. |  |
| 10/11 |  |  |
| 8:30 | Sample both. |  |
|  | (#2) pH adjusted to 5.91. (#3) pH adjusted to 5.92 |  |
|  | DO = 47% DO = 63%. |  |
| 3:30 | (#2) 600 g sclareol suspension added (150 g sclareol) |  |
|  | DO = 51% DO dropped to 50%. |  |
|  | (#3) 160 g paste added to (100 g sclareol) |  |
|  | DO = 62% DO dropped to 53%. |  |
| 10/12 |  |  |
| 9:00 | (#2) ph 5.79 (fermention adjusted per pH |  |
|  | (#3) ph 6.07) meter |  |
|  | Sample taken |  |
|  | 275 g paste added to (#3) - DO = 62% |  |
|  | 20 g NH₄NO₃ added to (#3) - 183 g sclareol |  |
| 9:30 | (#2) 20 g NH₄NO₃ added |  |
|  | 600 g sclareol suspension added - 150 g sclareol |  |
|  | DO = 72% |  |
|  | pH: 5.80. |  |
| 10:30 | (#2) DO = 67% pH = 5.80 |  |
|  | (#3) DO = 50% pH = 5.91 |  |
| 10/13 |  |  |
| 8:30 | (#2) DO = 75% (#3) DO = 67% |  |
|  | pH = 5.97 pH = 5.98 |  |
|  | Sample both. |  |
| 9:30 | (#2) Add 600 g sclareol suspension - 150 g sclareol |  |
|  | (#3) Add 250 g sclareol paste - 167 g sclareol |  |
|  | Add enough sterile water to #2 to bring volume up to 102. |  |
| 10/14 |  |  |
| 8:30 | (#2) DO = 75% ⎫ Sample both. |  |
|  | (#3) DO = 70% ⎭ |  |
| 10/17 |  |  |
| 8:30 | (#2) DO = 89% pH 6.31 |  |
|  | Culture is still granular in appearance. |  |
|  | (#3) DO = 82% pH 7.47 |  |
|  | Culture is blue-green color; slow granular fermentation. |  |

Produce was recovered from both fermenters by sieve w/o heating.

Later more material was recovered from (#3) broth by centrifugation.

Final product recoveries:
(#2) Crude: 570 g @ 54.33% purity—365 g sclareol
50–100 g sclareol was lost on top and sides of fermentor due to splashing and foaming.
(#3) Crude: 655 g @ 57.07%—correct—6734% (627 g recovered by sieve (28 g recovered by ctfg.) 441 g sclareolide A correction factor for purity of 1.18 was applied based on GC results w/out sclareolide.

Some green color remained throughout work-up of (#3).

EXAMPLE II(D)

2×10 L and 1×20 L batches.

0 20 L

| 500 g | crude sclareol (dry ground in blender) |
|---|---|
|  | TWEEN ® 80 |
| 34.0 g | NH₄NO₃ |
| 34.0 g | Yeast Extract |
| 17.0 g | KH₂PO₄ |
| 8.5 g | MgSO₄.7H₂O |
| 20.0 g | AF |
| 15 L | w/d-H₂O |

1 10 L

| 200 g | "clean" sclareol (acetone dissolved; recrystallized) |
|---|---|
| 100 g | TWEEN ® 80 |
| 20 g | NH₄NO₃ |
| 20 g | Yeast Extract |
| 10 g | KH₂PO₄ |
| 5 g | MgSO₄.7H₂O |
| 10 g | AF |
|  | to 9 L w/d-H₂O |

2 10L

Same as #2 except use crude sclareol.

11/7/88 Start-up

Inoculation:
1.0 L - 24 hr. shake flask on sugar for #1 and #2
2.0 L - 24 hr. for #0.
Inoculation pH adjusted to 5.8
All then inoculated between 9 and 10:00 AM.
0       1.0 L/min.; 300 rpm
1       0.5 L/min.; 603 rpm
2       0.5 L/min.; 597 rpm
At 4:00 P.M. add 2.0 L sterile H₂O to #0.

11/8 8:00

0 - DO = 12%
     pH = 5.8 meter 5.77 (adjusted)
1 - DO = 46%
     pH = 5.82 meter 5.78 (adjusted)
2 - DO = 44%
     pH = 5.80 meter 5.89 (adjusted)
(#1 and #2: Increase agitation to 630 rpm.)

3:30                                 4:30
0  pH 5.67      #0  770 g sclareol paste added =
    DO = 41%         308 g sclareol
1  pH 5.72      #1  383 g sclareol paste added =
    DO = 54%         153 g sclareol (clean)
3  pH 5.89      #2  390 g sclareol paste added =
    DO = 27%         156 g sclareol (crude)
                     Serious foam problem in #2.
4:50
Add 20 g NH₄NO₃ to #1 and #2; 40 g to #0.

11/9
8:00

0  pH 5.68       Meter 5.58 (adjusted)
    DO = 36%      Some back press developing
1  pH = 5.82     Meter 5.93 (adjusted)
    DO = 61%      No foam.
2  pH = 6.21     Meter 6.05 (adjusted)
    DO = 28%      Some foam.
Agitation was 530 rpm overnite; increased to 630
0 - pH singed to 6.5 @ 9:00 AM - stayed up all day.
2:00

0  pH 6.5        meter 5.86 (adjusted)
    DO = 50%
1  pH = 5.82     Meter 6.22 (adjusted)
    DO = 65%
2  pH = 5.91     Meter 5.94 (adjusted)
    DO = 67%

3:30
0  pH 5.67    #0  770 g sclareol paste
    DO = 1%        added = 308 g sclareol.
1  pH 5.72    #1  393 g Sclareol paste added =
    DO = 54%       153 g sclareol (clean).
3  pH 5.89    #2  390 g sclareol paste added =
    DO = 27%       156 g sclareol (crude)
                   Serious foam problem in
4:50
Add 20 g NH₄NO₃ to #1 and #2; 40 g to #0.

11/9
8:00

0   pH 5.68       Meter 5.58 (adjusted)
     DO = 36%      Some back press developing.
1   pH 5.82       Meter 5.93 (adjusted)
     D0 = 61       No foam.
2   pH 6.21       Meter 6.05 (adjusted)
     DO = 28%      Some foam.
Agitation was 530 rpm overnite; increased to 630
0 - pH singed to 6.5 @ 9:: AM - stayed up all day.
2:00

0   pH 6.5        Meter 5.86 (adjusted)
     DO = 50%
1   pH 5.82       Meter 6.22 (adjusted)
     DO = 65%
2   pH 5.91       Meter 5.94 (adjusted)
     DO = 67%

-continued

| | 4:00 | | |
|---|---|---|---|
| | pH | pH by Meter | DO |
| #0 | 5.70 | 6.03 | |
| #1 | 5.81 | 5.75 | 71% |
| #2 | 5.91 | 5.86 | 71% |

| | 4:30 | |
|---|---|---|
| #0 | Add 616 g sclareol paste (crude) = 246 g sclareol. | |
| #1 | Add 686 g sclareol paste (clean) = 274 g sclareol. | |
| #2 | Add 686 g sclareol paste (crude) = 274 g sclareol. | |

| | 11/14 9:00 |
|---|---|
| #0 | pH 6.22 |
| #1 | pH 5.91 |
| #2 | pH 7.15 |
| | #'s 9 and 2 are contaminated. |

| 9:30 |
|---|
| Terminate all - heat to 70° C. and hold for one hour. |

Note:
Over weekend antibiotics were added to #0 and #2 to combat contamination.
A large shot of AF was added by mistake to #1. All broths were held for wash up to recover sclareolide.

Product Recovery:
Products were recovered by sieving, dissolving in acetone and recrystallizing by adding water.

| Crude product yields | | | | |
|---|---|---|---|---|
| #0 | 605 g | Purity: | 91.6% | 554 g |
| #1 | 352 g + 18 g = 370 g | Purity: | 94% | 348 g |
| #2 | 465 g | Purity: | 94% | 437 g |

Purity is unknown pending development of a reliable analytical method.

EXAMPLE II(E)

| Fermentor #1 10 L (Inoculation for Fermentor #2) Organism: 8275 C (from freeze dried vial) sclareolide producer. | | |
|---|---|---|
| Broth: | | |
| 20.0 g | $NH_4NO_3$ | At time of inoculation |
| 20.0 g | Yeast Ext. | 100 g Glucose dded as 50% |
| 10.0 g | $KH_2PO_4$ | solution (sterilized separately) |
| 5.0 g | | |
| 10.0 g | AF | |
| to 9.5 | L w/d-$H_2O$ | |
| Parameters: | | |
| 25° C. | | |
| 1.0 L/min.; 0.36 back press | | |
| 525 rpm | | |
| pH 6.0 | | |
| Inoculation: | | |
| 1/13 | Slant - 100 ml shake flask, 0.5% glucose | |
| 1/15 | 100 ml Shake flask - fermentor. | |

Culture grown cg 24 hrs. then used as inoculion for fermentor #2. Portions also used for resting cell studies on 1/16/89.
Terminated on 1/16/89.

| Fermentor #2: 10 L Organism: IFF-8275C; source: freeze-dried vial. | |
|---|---|
| Broth: | |
| 20.0 g | $NH_4NO_3$ |
| 20.0 g | Yeast Extract |
| 10.0 g | $KH_2PO_4$ |
| 5.0 g | $MgSO_4.7H_2O$ |
| 150.0 g | sclareol |
| 75.0 g | TWEEN ® 80 |
| 10.0 g | AF |
| to 9.02 | w/d-$H_2O$. |
| Parameters: | |
| 25° C. | |
| 2.0 L/min ; no back press | |
| 430 rpm | |
| Initial pH 5.8; set pt. 5.8 | |
| Inoculation: | |
| 1/13 | Preparation as on p. 6868 |
| 1/15 | See p. 6868. |

| | 1.16 | |
|---|---|---|
| 9:00 A | 500 ml from fermentor #1 transferred via sterile lane to Ferm. #2. | |
| | 1/17 | |
| 10:45 A | Substrate depleted; DO increased from 15% to 60% in few minutes. Add 234 g paste - 156 g sclareol DO decreased to 12-15%. | |
| | 8:00 | |
| | Add 5.0 g $NH_4NO_3$ to #2. | |
| | 1/20 | |
| 9:00 | Terminate #2 and #3 - Continue #0. | |

Product was collected by sieve from both #2 and #3 400 wash used. Product was washed w/d-$H_2O$ on Buchner Funnel.
Recoveries:

| #2 | 779 g crude; purity: 50.45% - 393 g sclareol Plus: 40.56 g crude from fermentor rinse. Purity: 47.78% - 19.38 g sclareolide. Total sclareolide: 412.4 g - 95% conversion. In condition: 21.2 g sclareol was recovered Total recovery of added sclareol = 97.7% (as sclareolide or sclareol). |
|---|---|
| #3 | 491 g crude; purity: 42.46% - 208.5 g sclareolide correction factor: 1.035 - 216 g sclareolide Total of 311 g sclareol added 216.6 g sclareolide expected. 99.7% mole/mole recovery. |

Another 68.5 g crude product (rather wet) recovered from fermentor rinse water. Mostly sclareol by TLC.
Both products to be washed of by taking up in solvent recrystallizing from $H_2O$.

FIG. 2 is the GC-MS spectrum for the initial reaction mass in Example II(A). The peak indicated by reference numeral 21 is the peak for the sclareol which is a mixture (80:20) of the compounds having the structures:

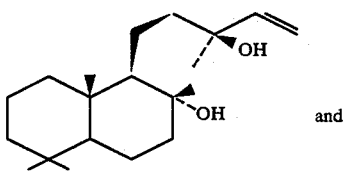 and

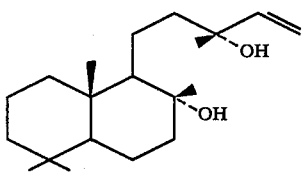

The peak indicated by reference numeral 20 is the peak for the standard, the compound having the structure:

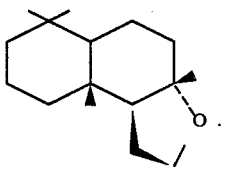

FIG. 4 is the NMR spectrum for the sclareolide produced according to Example II(D) having the structure:

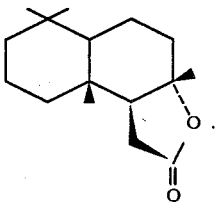

EXAMPLE III

Preparation of Sclareolide from Sclareol Using *Cryptococcus Albidus*, ATCC 20921

The same procedure is in Example II was used with the following details:

| Fermentor #3: 10 L | | |
|---|---|---|
| Broth | | Parameters |
| 20.0 g | NH4NO3 | 25° C. |
| 20.0 g | Yeast Extract | 1.02/min; no ack press. |
| 10.0 g | KH2PO4 | 430 rpm |
| 5.0 g | MgSO4.7H2O | Initial pH 5.8; Set pt 5.8 |
| 150.0 g | sclareol | |
| 75.0 g | TWEEN ® 80 | |
| 10.0 g | AF | |
| to 9.0 | w/d-H2O | |
| Inoculation: | | |
| 1/13 Slant - 100 ml shake flask - 0.5% sugar | | |
| 1/15 20 ml - 500 ml Fern. back; 0.5% sugar | | |
| 1/16 | | |
| 8:30 | Inoculation w/500 ml, 24 hr., shake flask | |
| 1/17 | | |
| #3 | Increase agitation to 530 rpm. | |
| #2 | Increase agitation to 530 rpm (DO 8%). | |
| 1/18 | | |
| 8:00 | | |
| | Substrate apparently depleted in #2 and #3. DO = 70% in both. | |
| #2 | Add 236 g paste - 157 g sclareol | |
| #3 | Add 241 g paste - 161 g sclareol | |
| 9:00 | | |
| #2 | Agitation increased to 630 rpm. | |
| 8:00 | | |
| | Add 5.0 g NH4NO3 to #2. | |

| Fermentor #3: 10 L |
|---|
| 1/20 |
| 9:00 |
| Terminate #2 and #3 - Continue #0. |
| Product was collected by sieve from both #2 and #3. 400 mesh used. Product was washed w/d-H2O on Buuchner funnel. |

| | Recoveries: |
|---|---|
| #2 | 799 g crude; purity: 50.45% - 393 g sclareol Plus |
| | 40.56 g crude from fermentor rinse. |
| | Purity: 47.78% - 19.38 g sclareolide |
| | Total sclareolide: 412.4 g - 95% mole/mole conversion. |
| | In addition: 21.2 g sclareol was recovered. |
| | Total recovery of added sclareol = 97.7% (as sclareolide or sclareol). |
| #3 | 491 g crude; purity: 42.46% - 208.5 g sclareolide |
| | correction factor: 1.035 - 216 g sclareolide |
| | Total of 311 g sclareol added 216.6 g sclareolide expected. |
| | 99.7% mole/mole recovery. |
| | Another 68.5 g crude product (rather wet) recovered from fermenter rise water. Mostly sclareol by TLC. |
| | Both products to be worked up further by taking up in solventd recrystallizing from H2O. |

EXAMPLE IV

Preparation of Sclareolide from Sclareol, Diol Intermediate and Diol Acetate

Reactions:

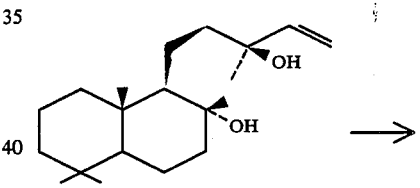

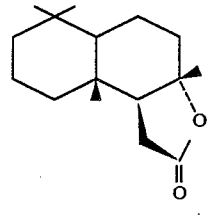

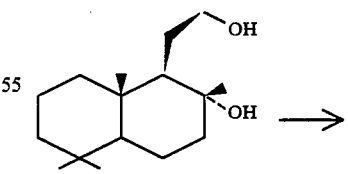

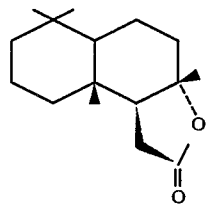

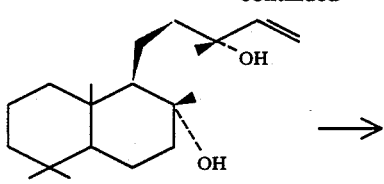

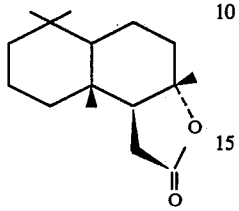

and

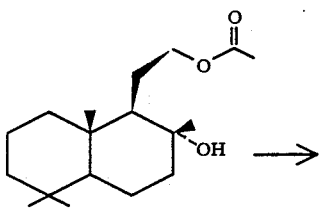

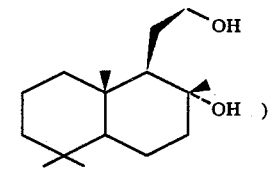

The following medium was prepared:
NH$_4$NO$_3$: 0.2%
KH$_2$PO$_4$: 0.1%
MgSO$_4$.7H$_2$O: 0.05%
Yeast Extract: 0.2%
Dextrose: 0.5%

A 10 liter fermenter was used with the following operating conditions:
Temperature: 25° C.
pH: 6
rpm: 430

Sterilization took place at 121° C. for 30 minutes.

The fermenter was inoculated with 100 ml of 48 hour grown cells on the same medium in the shake flask at 25° C. and 150 rpm.

After 24 hours, 200 ml aliquots were removed and centrifuged at 10,000 rpm for 10 minutes in a refrigerated centrifuge. The cells in each tube were washed twice with Butterfield's buffered phosphate:

Preparation:
Stock solution;
Monopotassium hydrogen phosphate 34.0 g
Distilled water 500.0 ml Adjust to pH 7.2 with about 175 ml/N sodium hydroxide solution; dilute to one liter and store.

Diluent:
Dilute 1.25 ml stock solution to 1 liter with distilled water. Prepare dilution blanks in suitable containers. Sterilize at 121° C. for 15 minutes. and then taken up in 100 ml of Butterfield's buffered phosphate. The pH is adjusted to 6 and then the material is transferred to a 500 ml flask. The supernatant liquid was also centrifuged at 10,000 rpm for 10 minutes, twice and 100 ml supernatant liquid was placed in each flask.

Compounds tested:
(a) Sclareol paste in TWEEN ® 80 (2:1)=Compound 1.
(b) Acetate (compound having the structure:

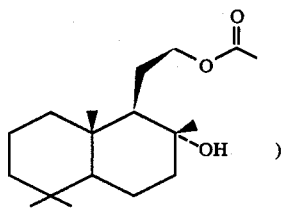)

mix in TWEEN ® 50 (1:1)=Compound 2.
(c) Diol paste (compound having the structure:

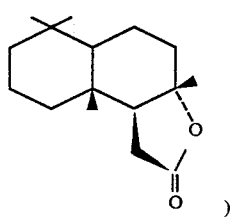)

in TWEEN ® 50 (1:1)=Compound 3.

300 ml Flasks containing 100 ml of buffer and cells (resting cells) were placed in shake incubators as 25° C. and 150 rpm and analyzed using TLC at 24, 48 and 72 hours against the standard known compound. In the following table:

P=Product (sclareolide having the structure:

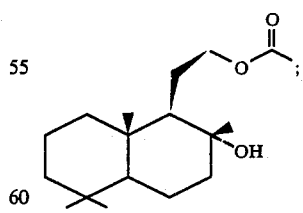)

S=Substrate (one of the compounds having the structures:

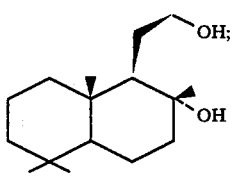

-continued

80:20 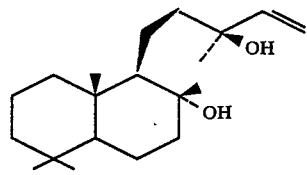

and

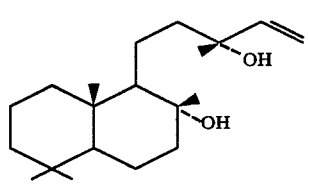

I = Intermediate (compound having the structure:

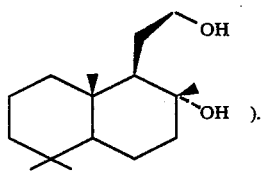 ).

T = Trace.

TABLE II

| Flask | Substrate | 24 Hrs. | 48 Hrs. | 72 Hrs. |
|---|---|---|---|---|
| 1 | 1 g of Compound (1) added | P + S + I | P + I | P + I |
| 2 | 1 g of Compound (2) added | P + TS + I | P + I | P + TI |
| 3 | 1 g of Compound (3) added | TP + S | P + S | P + TS |

Experiments as above using Compound (1), and an organic solvent instead of Buffer did not effect any transformation. The solvents tested were as follows:
Acetone;
Ethyl acetate;
n-Hexane;
Cyclohexanol;
Isopropanol;
Ethanol and
Toluene.

EXAMPLE V

Formation of Diol Intermediate from Sclareol Using *Bensingtonia Ciliata*, ATCC 20919

An example using the same procedure as Example I was carried out with the following specifications:
Fermenters set up as follows:

| Fermenter #0 - 20L | |
|---|---|
| Organism: | |
| IFF-8268C - Source: Freeze-dried vial Diol-producer. | |
| Broth: | |
| 40.0 g | NH$_4$NO$_3$ |
| 40.0 g | Yeast Extract |
| 20.0 g | KH$_2$PO$_4$ |
| 10.0 g | MgSO$_4$.7H$_2$O |
| 400 g | Sclareol emulsion (0.4 g sclareol/g) to 19 l w/d-H$_2$O. |

| Fermenter #0 - 20L | | |
|---|---|---|
| Parameters: | | |
| 25° C. | | |
| 300 rpm | | |
| 2.0 L/min. No B.P. | | |
| Initial pH = 5.8; set pH 6.0. | | |
| Inoculation Preparation: | | |
| 1/13 | Slant (prepared from freeze-dried vial) used to inoculate 2 × 500 ml flasks (Fernbach). | |
| | 2 and 500 ml cultures (48 hrs.) used in fermentor. | |
| 1/16 | 9:00 A | Inoculate DO set @ 95%. |
| 1/25 | 9:00 A | 10 g Yeast extract added. |
| 1/31 | Terminate. | Harvest solids w/400 mesh sieve. |

Ref. 6867D.

Product recovered by 400 mesh sieve was washed on Buchner Funnel, air dried and weighed.
89.7 g recovered
Additional product was recovered from the sieved broth by toluene extraction.
Product recovered: 12 g
Total product: 101.7 g
Total culture time: 15 days
Total substrate added: 160 g sclareol.

EXAMPLE VI

Large Scale Process For Producing Sclareolide

Reactions:

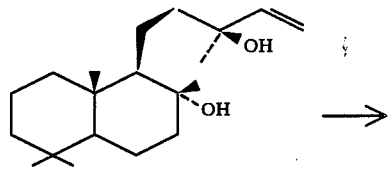

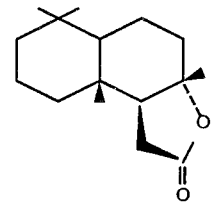

and

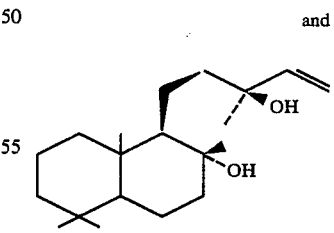

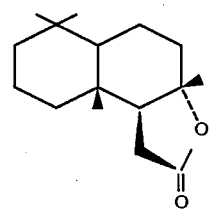

| Biotransformation Process Details |
|---|
| 1. Organism: *Cryptococcus albidus*, ATCC 20918 (IFF-8275C), isolated from soil sample from Mexico City using selective enrichment techniques. |
| 2. Inoculum Preparation: |
|   (a) Medium: Sy-broth |
|     Ammonium nitrate    0.2% |
|     Potassium dihydrogen phosphate    0.1% |
|     Magnesium sulfate heptahydrate    0.05% |
|     Yeast extract    0.2% |
|     *Dextrose    0.5% |
|     pH = 6.00 |
|     *A 50% solution of dextrose, sterilized separately and added just before inoculation. |
|   (b) Preparation Sequence |
|     i. A shake flask (500 ml containing 100 ml of Sy-broth is inoculated with a loopful of IFF-8275C and incubated at 25° C., 150 rpm for 48 hours. |
|     ii. 10 L of medium prepared in 14 L fermenter, sterilized 30 min. at 120° C., and cooled to 25° C., is inoculated with 100 ml of 48 hour shake flask culture. This inoculum is allowed to grow (25° C., pH 5.8, 530 rpm, 0.1 L/L/min aeration) for 24 hours. This inoculum is used at 5% (v/v) for laboratory or pilot plant production of sclareolide. |
| 3. Laboratory and Pilot Plant Production Process |
|   (a) Medium: |
|     NH$_4$NO$_3$    0.1% |
|     KH$_2$PO$_4$    0.1% |
|     MgSO$_4$.7H$_2$O    0.05% |
|     Yeast extract    0.2% |
|     Antifoam as needed |
|   (b) Fermentation Parameters |
|     Temp.:    25° C. + 0.1 |
|     pH:    =5.8 (control with 25% NaOH or 20% H$_3$PO$_4$) |
|     Agitation:    430–630 rpm (10 L); 200–250 rpm (100 L) |
|     Aeration:    0.1 L/L/min. |
|     Inoculum Level:    5% |
|   (c) Substrate Preparation |
|     Our studies have shown that the mode of addition and mesh size of sclareol powder have a great effect on this biotransformation. A powder of sclareol that passed through a 100 mesh sieve resulted in a very satisfactory conversion. However, in R & D due to lack of proper equipment, we settled on 80 mesh material. This particle size is sub-optimal; commercially we hope to achieve the proper mesh size using cryogenic grinding and automatic sifting. Sclareol powder is mixed with TWEEN ® 80 (2 parts sclareol to one part TWEEN ® 80) till a uniform paste is obtained. (This mixture was achieved with various mechanical mixers). This paste is added directly to the fermenter. On laboratory and pilot scale, this was done manually. On a larger scale pumping should be feasible. |
|   (d) Substrate Addition |
|     The course of fermentation is monitored using TLC. Based upon growth and substrate conversion, additional substrate is added. In most cases the following schedule is followed. |
|     Time    % of Fermenter Volume |
|     0 hrs.    2.25% paste (1.5% sclareol) |
|     24 hrs.    2.25% paste |
|     48 hrs.    2.25% paste |
|     72 hrs.    2.25% paste |
|     96 hrs.    Harvest |

This schedule is approximate and could be a little longer or shorter. The zero hour substrate may be added before or after sterilization. This will be determined by subsequent experiments.

Product Recovery

The product is a solid and may be recovered from the broth by one of the following methods:

(a) Centrifugation and washing with water.
(b) Filtration, (e.g., filter press) and washing with water.
(c) Sieving (400 mesh) and washing with water.

What is claimed is:

1. A biologically-pure culture of a microorganism selected from the group consisting of:
   (i) *Cryptococcus albidus* saito, skinner var. albidus, ATCC 20918; and
   (ii) *Cryptococcus albidus*, ATCC 20921.

2. A biologically pure culture containing a microorganism selected from the group consisting of:
   (i) *Cryptococcus albidus* saito, skinner var. albidus, ATCC 20918; and
   (ii) *Cryptococcus albidus*, ATCC 20921 each of said cultures being capable of producing the compound having the structure:

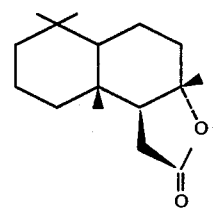

in a recoverable quantity upon the transformation of a compound selected from the group consisting of:

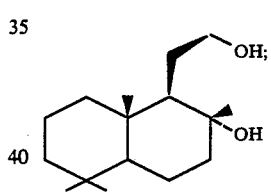

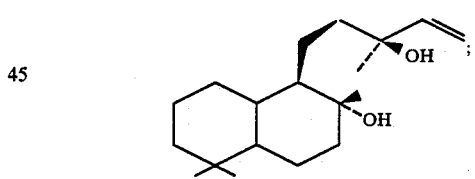

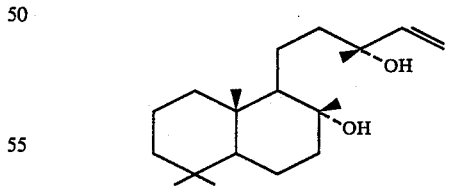

and

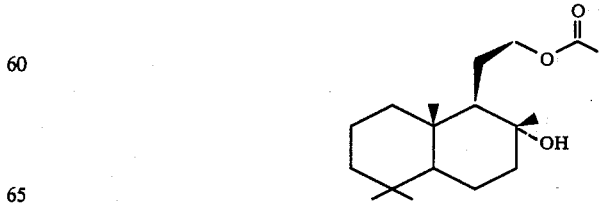

3. The culture of claim 1 in freeze-dried form.
4. The culture of claim 2 in freeze-dried form.

5. A process for preparing a lactone compound having the structure:

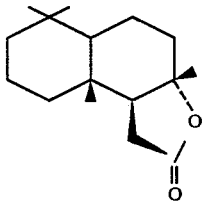

which comprises cultivating a microorganism selected from the group consisting of:

(i) *Cryptococcus albidus* saito, skinner var. albidus, ATCC 20918; and (ii) *Cryptococcus albidus*, ATCC 20921 to produce said lactone compound in a recoverable quantity by the transformation of at least one compound selected from the group consisting of:

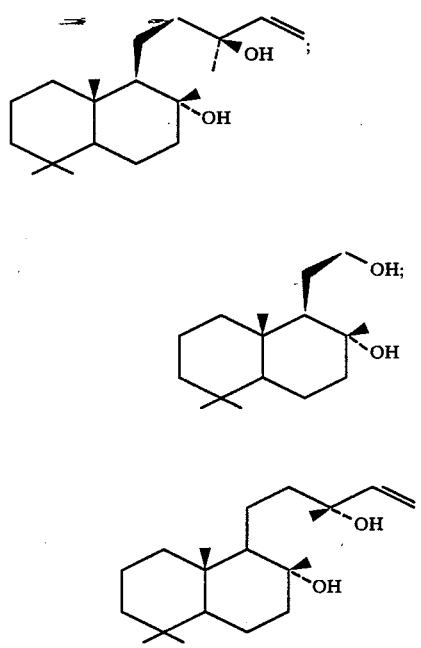

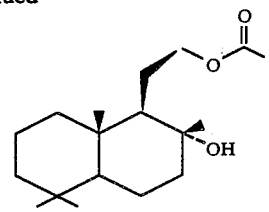

under aerobic conditions in an aqueous nutrient medium containing one or more compounds from said group and recovering said lactone.

6. The process of claim 5 wherein said lactone is recovered as a solid at ambient conditions.

7. A process for preparing a lactone compound having the structure:

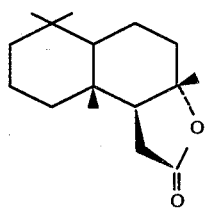

which comprises cultivating a microorganism selected from the group consisting of:

(i) *Cryptococcus albidus* saito, skinner var. albidus, ATCC 20918; and (ii) *Cryptococcus albidus*, ATCC 20921 to produce said lactone compound in a recoverable quantity by the transformation of at least one compound selected from the group consisting of:

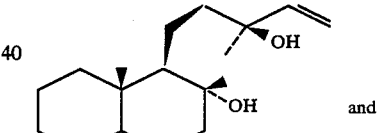 and

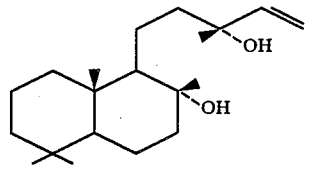

under aerobic conditions in an aqueous nutrient medium containing one or more compounds from said group and recovering said lactone.

8. The process of claim 7 wherein said lactone is recovered as a solid at ambient conditions.

* * * * *